(12) United States Patent
Salyer

(10) Patent No.: US 6,250,858 B1
(45) Date of Patent: Jun. 26, 2001

(54) TOOL DRIVER AND TOOLS THEREFOR

(75) Inventor: Paul E. Salyer, Warsaw, IN (US)

(73) Assignee: Othy, Inc., Warsaw, IN (US)

( * ) Notice: Subject to any disclaimer, the term of this patent is extended or adjusted under 35 U.S.C. 154(b) by 0 days.

(21) Appl. No.: 09/366,584

(22) Filed: Aug. 4, 1999

Related U.S. Application Data

(63) Continuation-in-part of application No. 09/049,275, filed on Mar. 27, 1998, now Pat. No. 5,980,170.

(51) Int. Cl.[7] .................................................. B23B 31/10
(52) U.S. Cl. .......................... 408/239 R; 279/37; 279/74; 279/106; 408/226; 408/231
(58) Field of Search ................................ 279/35, 37, 74, 279/106; 408/144, 226, 227, 231, 232, 239 R

(56) References Cited

U.S. PATENT DOCUMENTS

| 3,219,376 | * | 11/1965 | Peters | 294/16 |
| 4,585,369 | * | 4/1986 | Manesse et al. | 403/322 |
| 4,887,612 | * | 12/1989 | Esser et al. | 128/751 |
| 5,535,754 | * | 7/1996 | Doherty | 128/751 |
| 5,630,818 | * | 5/1997 | Del Rio et al. | 606/80 |
| 5,658,290 | * | 8/1997 | Lechot | 606/80 |
| 5,817,096 | * | 10/1998 | Salyer | 606/81 |
| 5,827,316 | * | 10/1998 | Young et al. | 606/185 |
| 5,954,463 | * | 9/1999 | Jore | 408/239 R |
| 5,980,170 | * | 11/1999 | Salyer | 408/239 R |
| 6,062,859 | * | 5/2000 | Filhol | 408/231 |

* cited by examiner

Primary Examiner—A. L. Wellington
Assistant Examiner—Monica S. Carter
(74) Attorney, Agent, or Firm—Krieg DeVault Lundy, LLP

(57) ABSTRACT

In the broader aspects of the invention, there is provided a new and improved tool driver having a shaft with a longitudinal axis and opposite ends and tools therefor. A boss is secured at one of said shaft ends by which the tool driver is connected to a rotary tool. A tool collate is secured at the other of the shaft ends by which the tool driver may be driven by a surgical hand piece having a chuck in which the collate may be positioned. The boss has a surface which engages the tool and positions the tool exactly coaxially of the tool driver. A latch mechanism is provided to hold the rotary tool on the boss, whereby the rotary tool is held exactly coaxially of the driver during use. The rotary tool which is used with the driver has a bottom tool driver opening which has the same dimensions as the boss of the tool driver of the invention. The boss thus fills the opening and the opening is complementary to the boss. The boss of the tool driver and the bottom tool driver opening of the tool are both positioned precisely coaxial of the axis of the tool and the longitudinal axis of the tool driver about which the cutting edges are precisely positioned and rotated.

31 Claims, 6 Drawing Sheets

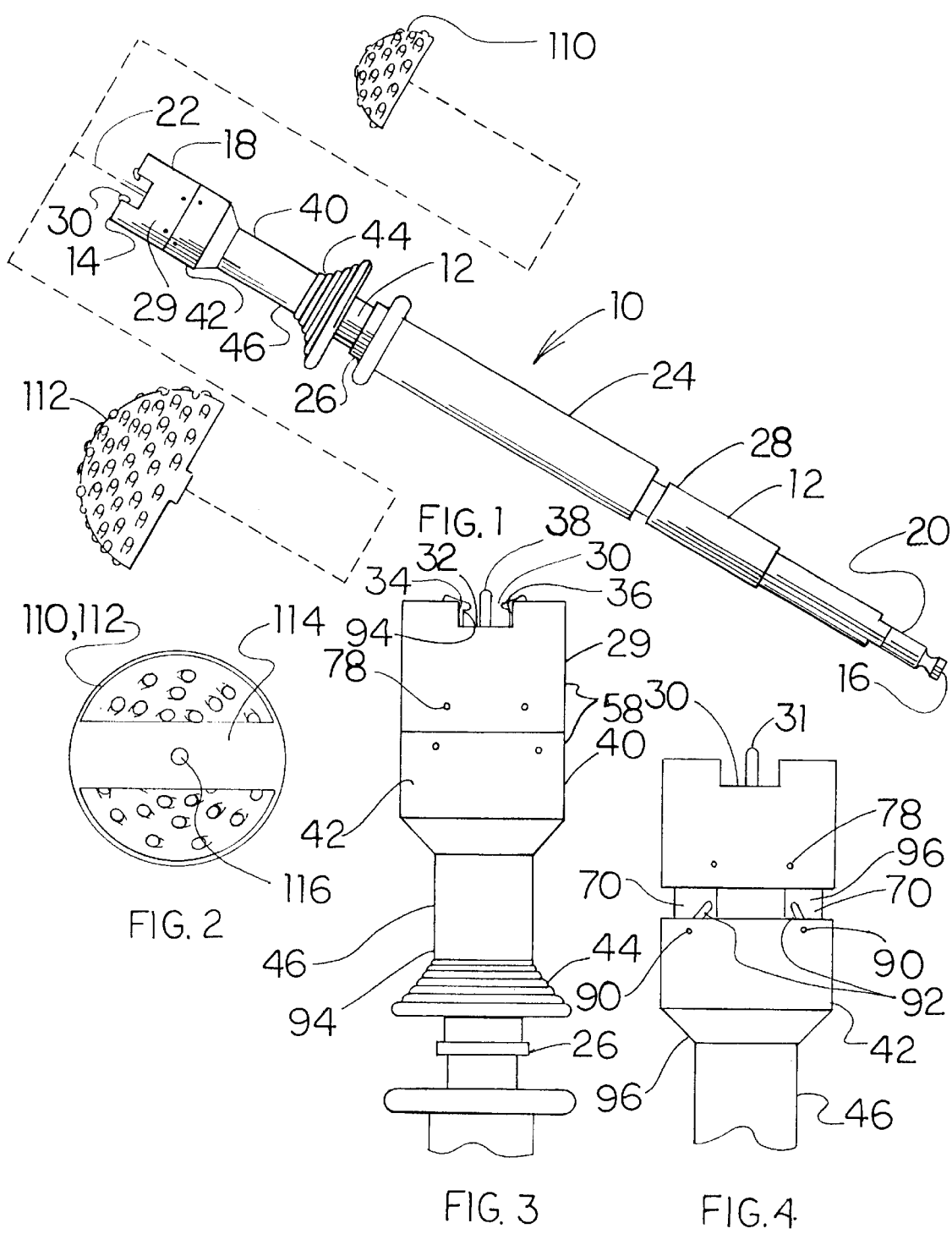

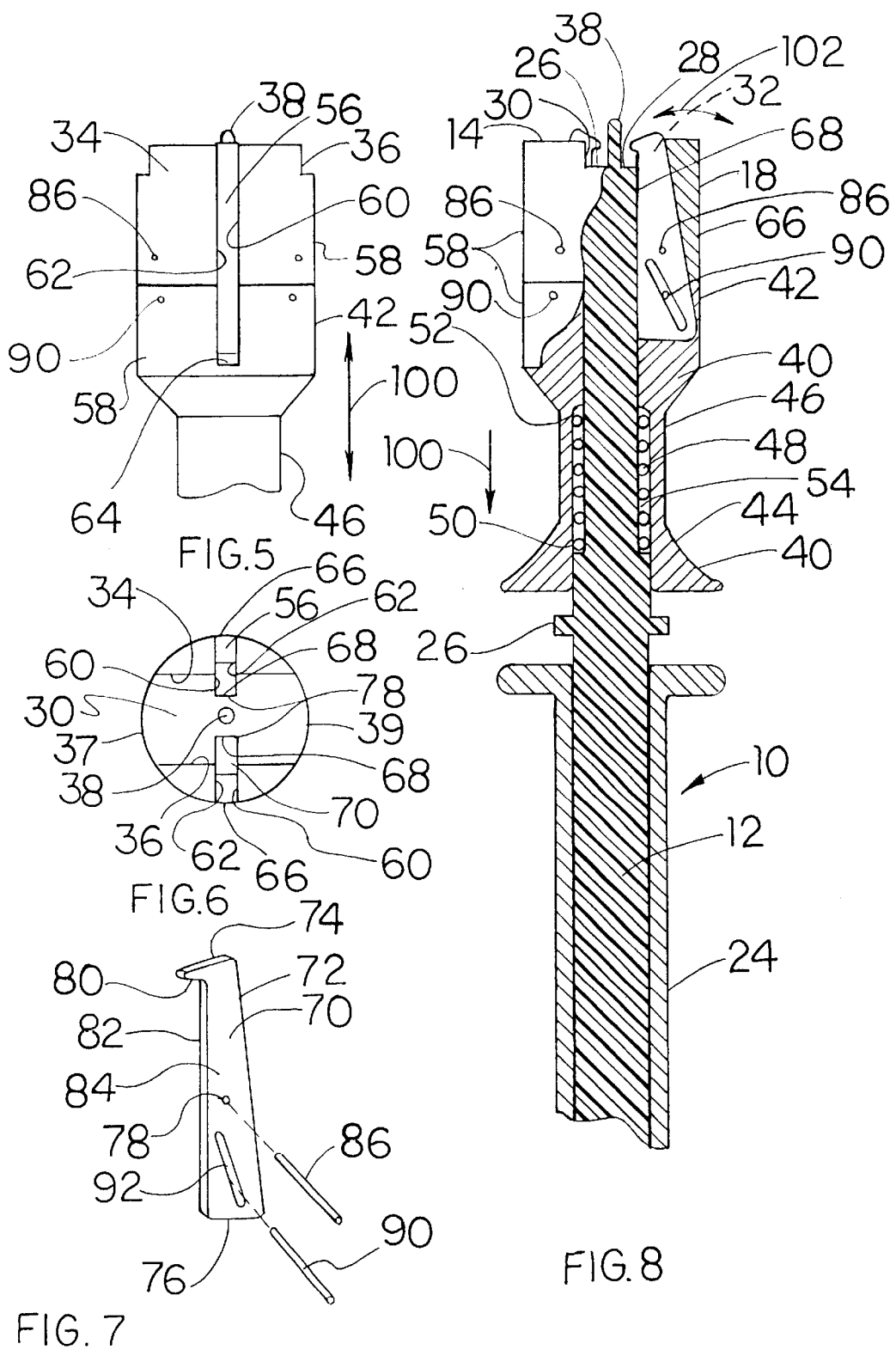

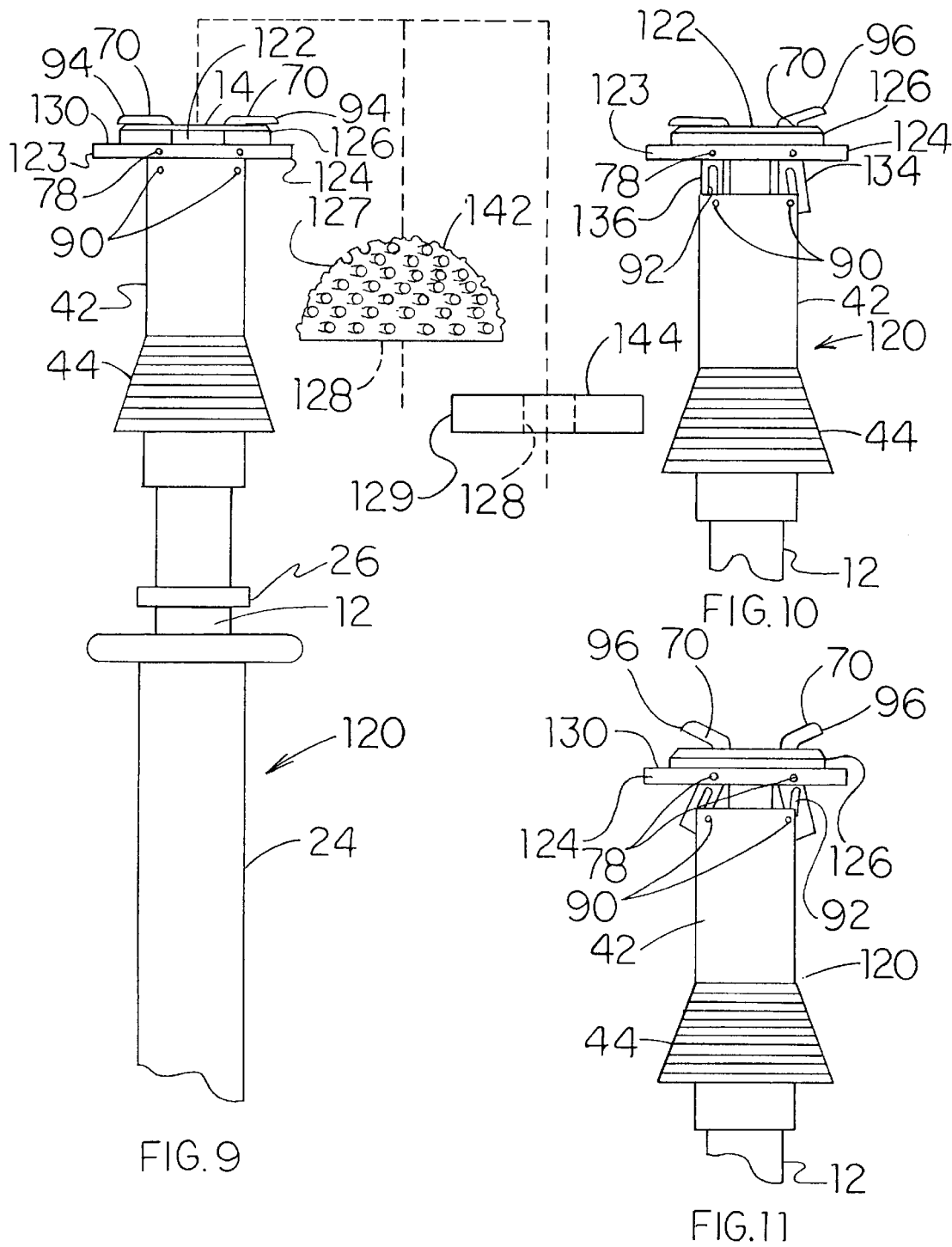

TOOL DRIVER AND TOOLS THEREFOR

This application is a continuation in part of U.S. patent application Ser. No. 09/049,275 filed on Mar. 27, 1998 entitled IMPROVED TOOL DRIVER by the same inventor, now U.S. Pat. No. 5,980,170.

BACKGROUND OF THE INVENTION

The present invention pertains to tool drivers and holders for rotary tools, and more particularly to a new and improved tool driver suitable for driving acetabular reamer cups and patella cutters and other surgical tools of any size which is easily cleaned and held and guided to rotate in true concentricity with the tool driver.

Patella cutters and acetabular reamer cups are surgical tools which are used in surgery for the insertion of artificial joints. Acetabular reamer cups are used to cut hemispherical cavities in pelvis bones for the insertion of artificial hip joints. Patella cutters are used to shape the underside of the patella or knee cap during knee replacement surgery. Patella cutters have a complex arrangement of precisely shaped cutting edges spirally arranged around the axis of rotation for cutting the patella. Acetabular reamer cups have a complex arrangement of cutting edges spirally arranged on a spherical surface around the axis of rotation of the cup. Both acetabular reamers and patella cutters perform better when rotated precisely about the axis around which these cutting edges are positioned by design. Additionally, precise tolerances cannot be achieved without precise axial rotation as designed.

It is therefore highly desirable to provide a new and improved tool driver. It is also highly desirable to provide a new and improved tool driver which can be used with acetabular reamer cups, patella cutters and like rotary tools. It is also highly desirable to provide a new and improved tool driver by which rotary tools may be driven about the tool driver's longitudinal axis with preciseness such that all of the cutting edges of the rotary tool function as designed.

Acetabular reamer cups also come in a full range of sizes. These sizes range from about 36 millimeters in diameter to about 72 millimeters in diameter. In the past, a specific tool driver could only be used with one or few of the sizes of available acetabular reamer cups. Thus, in any operating room there had to be several tool drivers for acetabular reamer cups. It is therefore also highly desirable to provide a new and improved tool driver by which acetabular reamer cups and patella cutters of all sizes can be driven.

Unique to some knee surgery and some hip operations is the utilization of milled bone, tissue and debris as filler to be placed between the artificial insert and the body to assist the healing process. Thus, acetabular reamer cups and patella cutters are mounted on tool drivers in a manner to collect such debris for such use. It is therefore, also highly desirable to provide a new and improved tool driver on which the rotary tools of the type which collect milled bone tissue and other debris for use as filler can be used.

In all surgery utilizing rotary tools, rotary tools such as driven by rotary tool drivers must be separable from their tool drivers to replace or sharpen as required. It may also be necessary to change tools during an operation, thus, both the rotary tools and the tool drivers must at times be cleaned, sterilized and reused. Thus, it is therefore also highly desirable to provide a new and improved tool driver which can be easily cleaned, sterilized and reused.

Some previous tool drivers grip the tool utilizing opposed pins, flanges and slots, or opposed spring loaded ball catches, or other such devices. These devices represent a problem in that the catches tend to trap dried blood and other debris which are very difficult to remove during a cleaning process. It is therefore also highly desirable to provide a new and improved tool driver which is simple in construction, easy to use and does not have opposed pins, flanges, slots and other devices in which to catch debris and render the tool driver difficult to clean, sterilize and reuse.

An additional problem is that unless tolerances of tools and tool drivers are made very close, at a greatly increased cost, there is considerable free play between the tool and the tool driver. This increased play increases the wear of the cutting edges, makes more difficult the positioning of the tool, renders the tool useless for holding close tolerances, requires the tool not to cut as designed, and there is no possibility of utilizing the rotary tool spinning precisely about its axis as designed. It is therefore, also highly desirable to provide a new and improved tool driver which allows the rotary tool to be utilized spinning precisely about its axis, as designed.

It is also highly desirable to provide a new and improved tool driver in which close tolerances can be held.

Finally, it is highly desirable to provide a new and improved tool driver which has all of the above desired features.

SUMMARY OF THE INVENTION

It is therefore and object of the invention to provide a new and improved tool driver and tools therefor.

It is also an object of the invention to provide a new and improved patella driver which can be used with both acetabular cups, patella cutters and like rotary tools.

It is also an object of the invention to provide a new and improved tool driver by which rotary tools may be driven about the tool drivers longitudinal axis with preciseness such that all of the cutting edges of the rotary tool function as designed.

It is also an object of the invention to provide a new and improved tool driver which acetabular reamer cups and patella cutters of all sizes can be driven.

It is also an object of the invention to provide a new and improved tool driver on which the rotary tools of the type which collect milled bone tissue and other debris for use as filler, can be used.

It is also an object of the invention to provide a new and improved tool driver and tools therefor which can be easily cleaned, sterilized and reused.

It is also an object of the invention to provide a new and improved tool driver which allows the rotary tool to be utilized spinning precisely about its axis as designed.

It is also an object of the invention to provide a new and improved tool driver which is simple in construction, easy to use and does not have opposed pins, flanges, slots and other devices in which to catch debris and render the tool driver difficult to clean, sterilize and reuse.

It is also an object of the invention to provide a new and improved tool driver and tools therefor in which dose tolerances can be held.

It is finally an object of the invention to provide a new and improved tool driver and tools therefor which has all of the above desired features.

In the broader aspects of the invention, there is provided a new and improved tool driver having a shaft with a longitudinal axis and opposite ends and tools therefor. A boss is secured at one of said shaft ends by which the tool driver is connected to a rotary tool. A tool collate is secured at the other of the shaft ends by which the tool driver may be driven by a surgical hand piece having a chuck in which the collate may be positioned. The boss has a surface which engages the tool and positions the tool exactly coaxially of the tool driver. A latch mechanism is provided to hold the rotary tool on the boss, whereby the rotary tool is held exactly coaxially of the driver during use. The rotary tool which is used with the driver has a bottom tool driver opening which has the same dimensions as the boss of the tool driver of the invention. The boss thus fills the opening and the opening is complementary to the boss. The boss of the tool driver and the bottom tool driver opening of the tool are both positioned precisely coaxial of the axis of the tool and the longitudinal axis of the tool driver about which the cutting edges are precisely positioned and rotated.

BRIEF DESCRIPTION OF THE DRAWINGS

The above-mentioned and other features and objects of the invention and the manner of attaining them will become more apparent and the invention itself will be better understood by reference to the following description of an embodiment of the invention taken in conjunction with the accompanying drawings wherein:

FIG. 1 is an exploded side view of the new and improved tool driver of the invention showing two sizes of acetabular reamer cups and patella cutters exploded therefrom, illustrating the versatility of the new and improved tool driver of the invention;

FIG. 2 is a rear view of the rotary tools illustrated in FIG. 1 showing the mounting bar thereof;

FIG. 3 is a fragmentary enlarged side view of the new and improved tool driver of the invention in which the latch is in its closed at rest position;

FIG. 4 is a view like FIG. 3 showing the latch of the invention in its open position;

FIG. 5 is a view like FIGS. 3 and 4 taken in a direction 90° from the direction of FIGS. 3 and 4;

FIG. 6 is a top view of the new and improved tool driver of the invention;

FIG. 7 is a perspective view of the latch member of the new and improved tool driver of the invention;

FIG. 8 is a fragmentary cross-sectional view of the improved tool driver of the invention taken in the direction of FIGS. 3 and 4 showing the latch mechanism of the invention;

FIG. 9 is an exploded fragmentary side view of a modified version of the new and improved tool driver of the invention like FIG. 1 having a hexagonal boss thereof, and showing an acetabular reamer cup and a patella cutter exploded therefrom;

FIG. 10 is a view like FIG. 4 showing the modified version of the latch of the new and improved tool driver of the invention shown in FIG. 9 having a square or rectangular boss thereon with the latch of the invention in its open position;

FIG. 11 is a view like FIG. 4 of another modified version of the latch of the new and improved tool driver of the invention shown in FIG. 9 having a circular boss thereof with the latch of the invention in its open position;

DESCRIPTION OF A SPECIFIC EMBODIMENT

Figures 12, 13, 14:
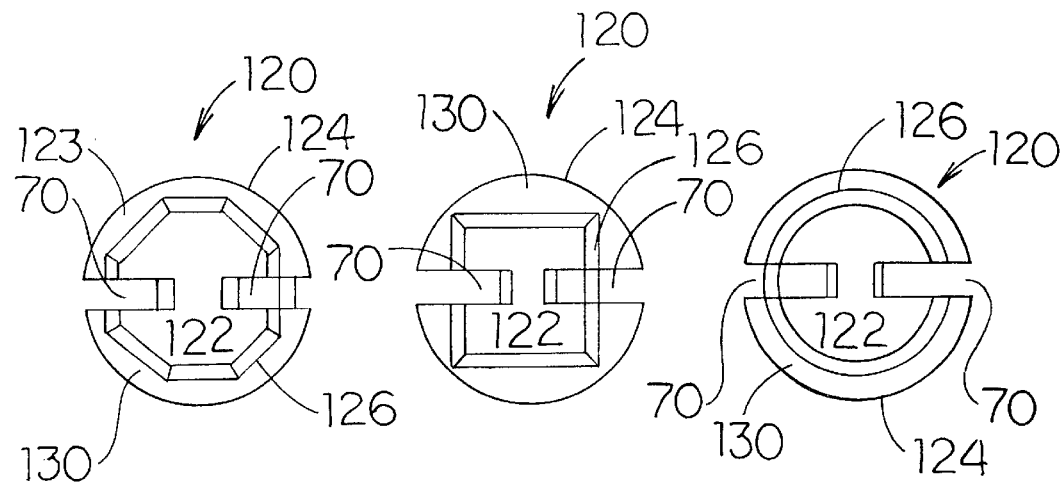
FIGS. 12, 13 and 14 are top views of the new and improved tool driver of the invention shown in FIGS. 9, 10 and 11, respectively, with the end plate removed.

The tool driver 10 comprises a shaft 12 having opposite ends 14, 16. At end 14, a boss 18 is secured to shaft 12. At end 16, a tool collate 20 is secured to shaft 12. Shaft 12 has an elongated axis 22 about which both boss 18 and collate 20 are positioned and rotated during use. Boss 18, collate 20 and shaft 12 are coaxial and aligned in an end to end relation. Coaxially positioned on the shaft 12 is a handle 24. Handle 24 is free to rotate around the shaft 12. The handle 24 is positioned between a pair of spaced apart rings 26, 28 which are secured to the shaft 12.

Boss 18 has an exterior distal surface 29 and a groove 30 cut therein which extends transversally of the shaft 12 across end 14 between diametrically opposite portions of boss 18. Groove 30 has a bottom 32 and upstanding sides 34 and 36. A centering pin 38 is secured to shaft 12 and extends coaxially thereof outwardly of bottom 32. In the specific embodiment illustrated, pin 38 is equidistant between groove walls 34, 36 and equally positioned between opposite groove ends 37, 39 and extends coaxially beyond end 14.

Positioned on shaft 12 between the boss 18 and ring 26 is a latch actuator 40. Latch actuator 40 is slideable axially along shaft 12 and, in the specific embodiment illustrated, is generally coaxial of the shaft 12. Latch actuator 40 has a boss end 42 and a thumb trigger 44 spaced apart by a mediate portion 46 which are formed integrally as a single piece. Latch actuator 40 is resiliently urged against boss 18 as shown in FIG. 8 by a spring 48 which is coaxially positioned on shaft 12 between step 50 on shaft 12 and actuator 40.

Boss end 42 also has an exterior surface 58 which when boss end 42 is urged against boss 18 is a continuation of the exterior surface 58 of boss 18. Spring 48 is compressed between an annular step 50 in shaft 12 and the bottom 52 of an annular groove 54 cut into mediate portion 46 between boss portion 40 and thumb trigger 44 of actuator 40 as shown in FIG. 8.

Both boss 18 and boss end 42 of actuator 44 have latch slots 56 formed therein which extend from the exterior surface 58 of boss 18 and boss end 42 inwardly. Latch slots 56 each have opposite sides 60, 62, a bottom 64, an open side 66, and a closed side 68. See FIGS. 5, 6 and 8. Positioned within these latch slots 56 are latch pieces 70 such as illustrated in FIG. 7.

Each latch piece 70 has an elongated body 72 having opposite ends 74, 76, a medial pivot bushing 78 and a hook portion 80. Latch pieces 70 are made from sheet stock and cut to have opposite ends 74, 76, and opposite sides 82, 84. Pin 86 extends through a bushing 78 and into boss portion 18 when latch pieces are positioned within slots 56. A follower 90 is extended through an angular slot 92 and secured to boss end 42 of actuator 40.

Referring to FIGS. 6 and 8, latch members 70 are shown in their "at rest" and extended position 94 in which hook portions 80 extend into groove 30 adjacent to pin 38. Hook portions 80 are moveable between their "at rest" position 94 shown in FIGS. 3, 6 and 8 and their retracted position 96 shown in FIG. 4. Actuator 40 is slideable axially of shaft 12 as indicated by the arrow 100 against the resiliency of the spring 48 into its retracted position 96 shown in FIG. 4. When moving actuator 40 away from boss 18, follower 90 moves in slot 92 which pivots latch member 70 about pivot 78 as indicated by arrow 102 shown in FIG. 8 from their "at rest" position 94 to their retracted position 96 in which the latch members are completely within boss portion 18 and not within groove 30 as shown in FIG. 4.

The rotary tools useful with the tool driver of the invention may include a variety of different types. Both acetabular reamer cups 110 and patella cutters 112 of various sizes ranging from 36 millimeters in diameter to 72 millimeters in diameter may be utilized. Each of these rotary tools have a mounting bar 114 secured to the tool. The mounting bar 114 has dimensions complementary of groove 30 and a hole 116 coaxial of the tool 110, 112 and dimensions complementary of pin 38.

Figures 15, 16, 17:
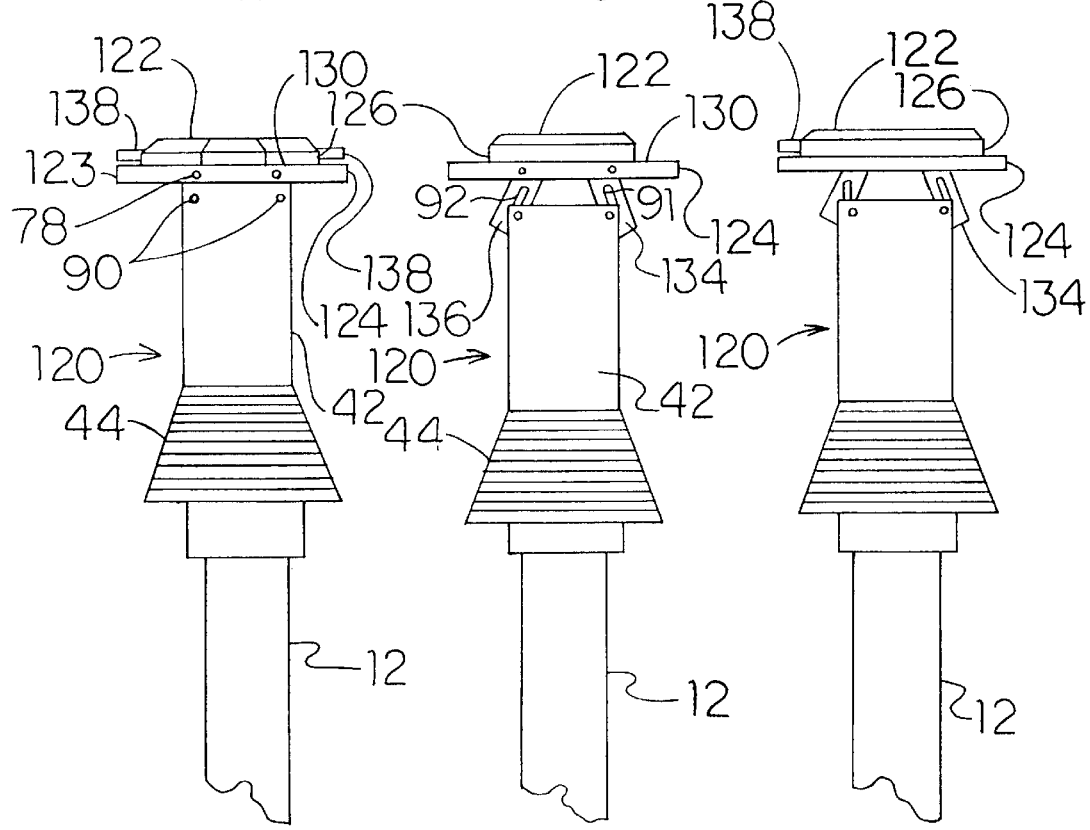
FIG. 15 is a fragmentary side view of still another modified version of the new and improved tool driver of the invention utilizing a hexagonal boss such as shown in the version of FIGS. 9 and 12, but utilizing latch pins shown in their extended position.
FIG. 16 is a fragmentary side view of still another modified version of the new and improved tool driver of the invention utilizing a square or rectangular boss such as shown in FIGS. 10 and 13, but utilizing dual latch pins extending from the boss shown in their retracted position.
FIG. 17 is a fragmentary side view of still another modified version of the new and improved tool driver of the invention utilizing a circular boss like that shown in FIGS. 11 and 14, but utilizing latch pins extending from the boss, only one of the latch pins being movable, the movable latch pin of the pair being shown in its retracted position.
Figure 18:
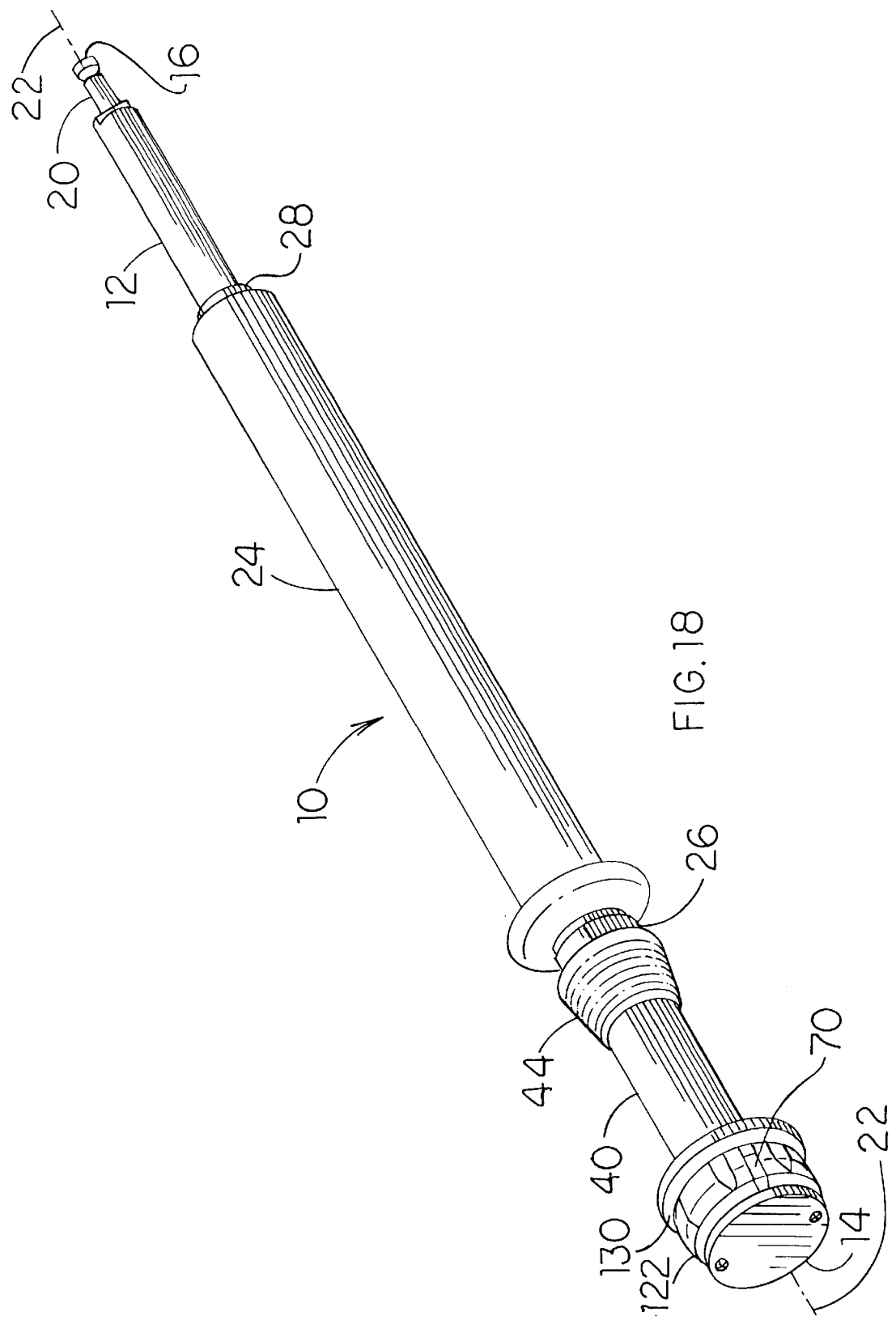
FIG. 18 is a perspective view of the new and improved tool driver of FIGS. 9 and 12 of the new and improved tool driver of the invention showing the latch of the invention in its at rest and extended position with the end plate in place.

Referring to FIGS. 1–17 and more particularly to the version 10 shown in FIGS. 1–8, and the versions 120 shown in FIGS. 9–17, each of the versions of the invention shown in FIGS. 1–8, 9, 11, 15 and 16 include a pair of moveable latch pieces 70, or have a single moveable latch piece 70 such as shown in the versions 120 of FIGS. 9, 10 and 17. In the embodiments shown in FIGS. 9, 10 and 17, the right hand latch piece 70 which is also given the reference numeral 134 is moveable and functions similarly to the movable latch pieces 70 above described. The left hand latch piece 70, 136 is immovable and may be made immovable by either securance of the latch piece 70 to the boss 122 or the provision of an axially extending slot 92 in which the follower 90 moves axially of the shaft 12 as shown in FIGS. 10 and 17 rather than angular of the axis 22 of the shaft 12 as shown in FIGS. 4 and 8.

In contrast, the embodiment 120 shown in FIGS. 9, 11 is identical to the embodiment 120 above described and shown in FIGS. 9, 10 except that both latch pieces 70 rather than only a single latch piece 70 are movable between an-rest position 94 shown in FIG. 9 and a retracted position 96 as shown in FIGS. 10 and 11, respectively.

In all of the versions 120 shown in FIGS. 9–18, boss 18 is replaced with a boss 122 and a disc shaped base 123 having a peripheral or outer dimension 124 larger than the boss 122 and thereby defining a surface 130 which faces outwardly of the tool driver 10. In these versions 120, the bosses 122 may be of any geometrical shape in cross-sections taken transversely of the axis 22, and is shown in FIGS. 9, 12 and 15 to be hexagonal, FIGS. 10, 13 and 16 to be square or rectangular, and in FIGS. 11, 14 and 17 to be circular. In each of the versions, latch pieces 70 function as above described to clamp the bottom of tools 127 and 129 to the surface 130.

In those versions 120 such as shown in FIGS. 15 and 16 which utilize pins but which have a boss 122 which fits into a complementary shape bottom opening 128 of a tool such as tools 127, 129, pins 138 merely overlay the tool bottom and clamp the tool bottom to surface 130. In this version, tool bottom is positioned between pins 138 and surface 130 and function solely to hold the tool bottom onto the boss 122.

Referring to FIGS. 15–17, there is shown a version 120 in which the portions 80 of the latch pieces 70 are in the form of moveable or immovable pins 138. Moveable pins 138 have all of the other features of latch pieces 70 including latch piece body 72, follower slot 92 and the like as shown in FIG. 7. Immovable pins 138 may have all of the other features of latch pieces 70 but with a axially extending slot 92 as shown in FIGS. 10 and 17 (rather than a slot 92 angularly disposed to axis 22) or a pin 138 which is positioned within a bore drilled in boss 122 and secured therein.

In the specific embodiment illustrated in FIGS. 9, 14, latch pieces 70 or pins 138 are used exclusively to keep the tools 142 or 144 from rotating independently of the tool driver 10, 120 as that version has a boss 122 which is circular in cross sections taken transversally of longitudinal axis 22.

In all other versions of the tool driver 10, 120 of the invention, latch pieces 70 are not relied upon to prevent rotation between the tool piece and the tool driver as the bosses 18, 122 fit into a complementary bottom opening 128 or have a bar 114 which fits within groove 30 and the engagement between the bar 114 and the sides 34, 36 of the groove 30 or the engagement between the boss 122 and the bottom opening 128 is used to prevent the rotation of the tool relative to the tool driver 10, 120 of the invention.

Figure 21:
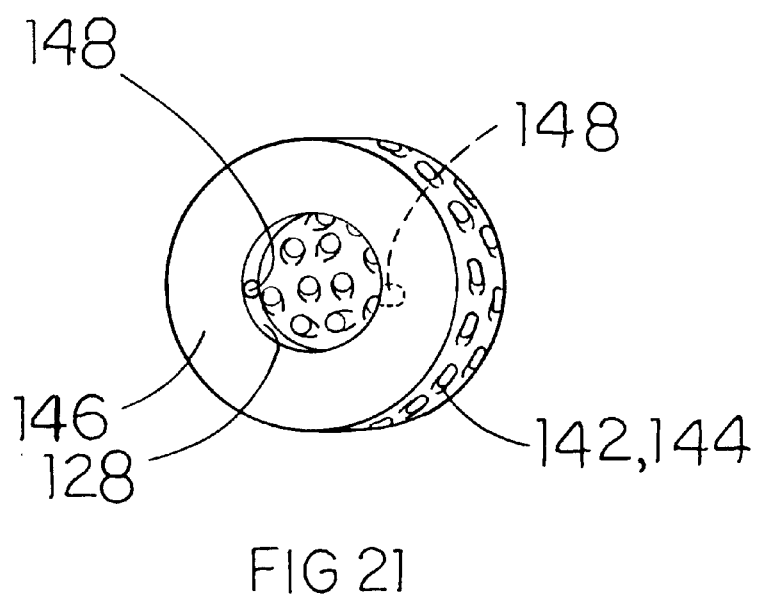
FIG. 21 is a perspective view of another version of the rotary tools illustrated in FIG. 9 showing the circular bottom opening and the diametrically opposite pin openings adjacent the periphery of the bottom opening to be used with the tool driver shown in FIGS. 11, 14 and 17.

In those embodiments utilizing a circular boss 122 and pins 138, pins 138 are positioned within holes 148 in the tools 142, 144 with which the tool driver 10, 120 is used as shown in FIG. 21 to prevent the tool 142, 144 from rotating independently of the tool driver 10. In this version, tools 142, 144 each have diametrically opposite holes 148 adjacent the periphery of bottom hole 116 in which pins 138 are positioned.

Figure 19:
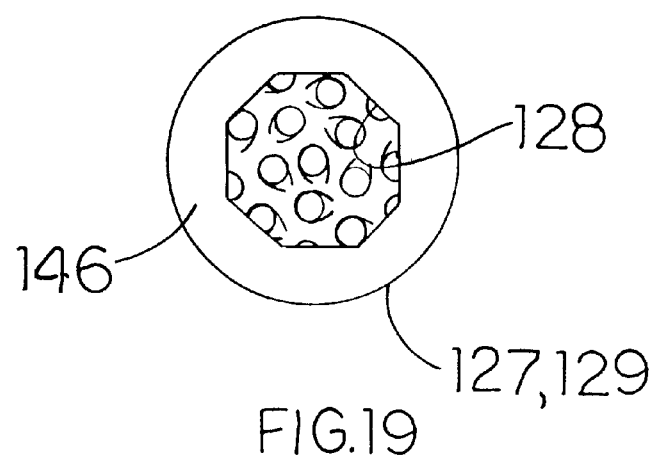
FIG. 19 is a rear view of one version of the rotary tools illustrated in FIG. 9 showing the bottom hexagonal opening of the tools to be used with the tool driver shown in FIGS. 9, 12 and 15.

Referring to FIG. 19, there is shown the bottom of tool 127, 129 having an opening 128 designed for use with the tool drivers illustrated in FIGS. 9, 12 and 15. Bottom opening 128 has both a shape and size which is complementary to the boss 122 such that boss 122 when fitted into opening 128 not only positions the tools 127, 129 coaxial of the axis 22 of the tool driver but also prevents the tools 127, 129 from rotating about the axis 22 independently of the tool driver by the engagement of the tool bottom with the boss 122.

Figure 20:
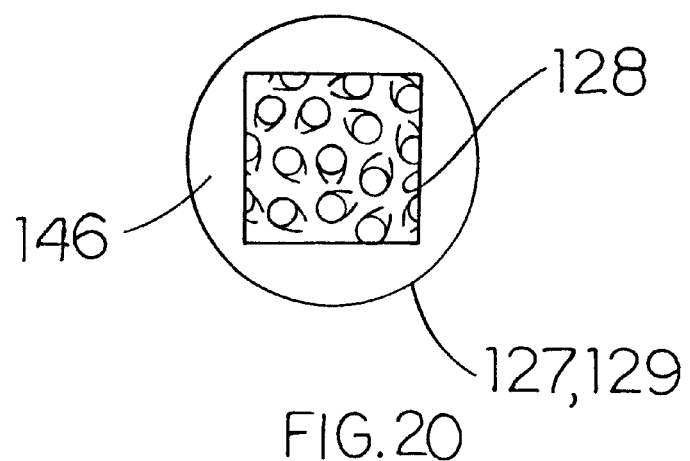
FIG. 20 is a rear view of still another version of the rotary tools illustrated in FIG. 9, showing the square or rectangular bottom opening of the tools to be used with the tool driver shown in FIGS. 10, 13 and 16.

Referring to FIG. 20 there is shown the bottom of another set of tools 127, 129 which are designed for use with the tool drivers illustrated in FIGS. 9, 10, 13 and 16. In this embodiment, bottom opening 128 is shown to be square or rectangular rather than hexagonal. Bottom opening 128 is both shaped and sized to be complementary to the boss 122 of the tool driver 120. When the tools 127, 129 are positioned on the tool driver 120, boss 122 fits within the bottom hole 128 to position the tools 127, 129 coaxially of the tool driver 120 and its axis 22. The upstanding sides of the boss 122 engage the sides of the bottom opening 128 to prevent the tools 127, 129 from rotating independently of the tool driver 120.

In both of the tools 127, 129 illustrated in FIGS. 19 and 20, the tools 127, 129 are held onto the tool driver 120 and against boss surface 130 to prevent it from moving axially thereof by either the latch pieces 70 or the pins 138. Both the hook portions 80 and pins 138 are positioned so as to be spaced apart from surface 130 with bottom 146 therebetween.

Referring now to FIG. 21, tools 142, 144 for use with tool driver 120 as shown in FIGS. 9, 14 and 17, are shown to have a tool bottom 146 and a tool opening 128 therein. Tool opening 128 in this version, is circular. In this version, the boss 122 is complementary with the bottom hole 128. When boss 122 is positioned within the bottom hole 128 of the tools 142, 144, the tools 142, 144 are coaxially positioned with the tool driver 120 on its axis 22. Without more, the tools 142, 144 may rotate independently of the tool driver 120; and thus, the tools are provided with bores 148 in the bottom 146. Bores 148 are diametrically opposite each other on the same axis, and extend transversely of the axis 22. Bores 148 receive the pins 138 so as to not only hold the tools 142, 144 against surface 30 but also prevent the tools 142, 144 from rotating independently of tool driver 120.

In a specific embodiment, shaft 12, actuator 40, and rotary tool such as the acetabular reamer cups 110, 127, 142 and patella cutters 112, 129, 144 are each made of stainless steel. The shaft has a diameter from about 0.0485 inch to about 0.505 inch, the actuator 40 has a diameter from about 1.125 inches to about 1.135 inches, shaft 12 has an axial length from about 7 inches to about 7.125 inches, actuator 40 has an axial length from about 2 inches to about 2.0625 inches, slot groove 30 has a width from about 0.495 inch to about 0.505 inch, and a length from about 1.129 inches to about 1.130 inches. Slots 56 have an axial length from about 1.215 inches to about 1.225 inches, a width from about 0.125 inch to about 0.135 inch, and a thickness from about 0.410 inch to about 0.420 inch. Latch pieces 70 have a length from about 1.250 inches to about 1.900 inches, a width from about 0.120 inch to about 0.125 inch, and a thickness from about 0.200 inch to about 0.220 inch. Bushing 86 is about 0.062 inch to about 0.070 inch from end 74 and from about 0.062 inch to about 0.070 inch from side 82. Angular slot 92 is about 0.062 inch to about 0.065 inch in thickness and is from about 0.850 inch to about 0.860 inch from end 76 and angles from about 17 inches to about 17.5 inches from sides 82 and 84. Mounting bar 114 has a thickness from about 0.120 inch to about 0.130 inch, and a width from about 0.490 inch to about 0.495 inch. Its length is dependent upon the diameter of the rotary tool. Hole 116 is positioned at its center an equal distance between its opposite ends and sides and has a diameter of about 0.125 inch. Pin 38 has a diameter from about 0.124 inch to about 0.125 inch.

In a specific embodiment of version 120, outer portion 126 of boss 122 has a diameter of about 1.250 inches, inner portion 124 of boss 122 has a distance between flats of about 1.018 inches whether boss 122 is square or hexagonal. Boss 122 has an axially length of about 0.3 to about 0.4 inches of which inner boss has a thickness of about 0.125 inches. Boss 122 may have a chamfer of about $10^0$ extending from end 18 a partial thickness of outer boss portion 124 in the direction of axis 22.

In operation, the improved tool driver 10 of the invention can be utilized to tightly grip and easily receive rotary tools such as acetabular reamer cups 110 and patella cutters 112 of a variety of sizes. The rotary tools 110, 112 each have an open bottom across which is secured mounting bar 114. The rotary tool of choice may be secured to tool driver 10 by grasping the tool driver 10 by the handle 24. In this position handle 24 is held between the fingers and the palm of a hand and the thumb can be positioned on the trigger 44. From this position, the thumb can move the actuator 40 against the urging of the spring 48 axially towards the handle 24. This movement of the actuator 40 from its at rest position 94 pivots the latch pieces 70 out of the groove 30 allowing the mounting bar 114 of the rotary tool to be positioned in the groove 30. Releasing the trigger 44 and allowing the spring 48 to move the actuator 40 in the opposite axial direction against the boss portion 18 of the shaft 12 pivots the latch pieces 70 so as to position to hook portions 80 within the groove 30 and to hold mounting bar 114 in groove 30 and the rotary tool onto end 14 of shaft 12.

Specifically, the actual movement of the actuator 40 towards the handle 24, causes the followers 90 to move within the latch slots 56 within the latch pieces 70. The movement of the follower 90 in the latch slots 56 generally in a direction towards the handle 24 causes the latch pieces to pivot about the pivot pin 78 and to move the hook portions 80 radially outwardly of the shaft 12 and to remove them from the groove 30. The movement of the latch pieces 70 is all within the latch slots 56, within the boss 18 and within the boss portion 42 of actuator 40. Thus, no portion of the latch piece 70 protrudes from the boss 18 of the shaft 12 or the boss portion 42 of the actuator 40.

Similarly, the movement of the actuator 40 away from the handle 12 toward end 14 of the shaft 12 by the spring 48 moves the follower 90 within the latch slots 56 of the latch pieces 70 generally axially away from the handle 24. This movement of the follower 90 pivots the latch pieces 70 about the pivot pin 78 to move the hook portions thereof radially inwardly and to position the hook portions within groove 30.

The cross-sectional dimensions of the groove 30 taken through the hook portions of the latch piece 70 are complementary to the cross-sectional dimensions of the mounting bar 114 of each of the rotary tools 127, 129 used with the tool driver 10 of the invention.

In a specific embodiment, this cross-section measures from about 0.250 inch about 0.270 inch plus or minus 0.005 inch by 0.505 inch plus or minus 0.005 inch of the groove 30. Similarly, the mounting bar cross-section is dimensioned as 0.500 inch plus or minus 0.005 inch by 0.200 inch plus or minus 0.005 inch. Thus exactly fitting mounting bar 114 in groove 30 with tolerances of plus or minus 0.005 inch.

Similarly, mounting bar hole 116 and pin 38 have a diameter which are complementary to each other. In a specific embodiment, pin has a diameter of 0.125 inch plus or minus 0.001 inch and hole 116 has a diameter of 0.128 inch plus or minus 0.001 inch.

Therefore each rotary tool used with the improved tool driver 10 is exactly coaxially positioned on shaft 12 within the tolerances of plus or minus 0.005 inch.

Similarly, the improved tool driver 120 can be utilized to tightly grip and easily receive rotary tools 127, 129, 142, 144 of a variety of sizes. These rotary tools each have a bottom opening 128 which is complementary in size and shape to boss 122 as above described. In all embodiments, the cups and cutters 127, 129, 142, 144 are secured from rotation relative to the boss 122 either by the latch pieces 70 or the pins 138 or by the engagement between bottom opening 128 and the boss 122.

Similarly, hook portions 80 of latch pieces 70 or pins 138 of latch pieces 70 in most embodiments function to clamp rotary tools 110, 112, 127, 129, 142, 144 against bottom 32 of groove 30 of version 10 or against surface 130 of versions 120 of the tool holder of the invention. Thus, in those versions with which cups 127 and cutter 129 are utilized, the bottom 146 in which bottom opening 128 is positioned has a thickness which is essentially the same as the distance between hook portions 80 of latch pieces 70 and surface 130 when latch pieces 70 are in their at-rest position 94. Such is also true as to the distance between pins 138 and surface 130 when cups 127 and 129 are utilized.

When utilizing cups 142 and cutter 144 in which holes for pins 138 are positioned adjacent the periphery of bottom hole 128, it is only essential that pins 138 and holes 148 are coaxially when the bottom of the cup is on boss 122 and contiguous with surface 130.

In those versions of tool driver 10, 120 in which both of the latch pieces are movable, tools 110, 112, 127, 129 and 142 and 144 are merely positioned on bottom 32 or surface 130 when the latch pieces 70 are in their retracted position 96 and are clamped against surface 32 or 130 by the latch pieces 70 when moved into their at-rest position.

In those embodiments in which one of the latch pieces 70 are stationary as shown in FIGS. 10 and 17, tools 110, 112, 127, 129, 142, 144 are first engaged by the nonmoveable latch piece 70 or pin 138 and then moved against surface 32 or surface 130 when the other latch piece 70 or pin 138 is in its retracted position 96 and is similarly clamped against surface 32 or 130 by moving the moveable latch piece 70 or pin 138 into its at-rest position.

In those embodiments utilizing tools 142, 144, pins 138 must be positioned in the opening 148 in the tools and the tools slid onto surface 130 when the pins 138 are in their retracted position 96. The cup 142 or cutter 144 is then fully moved against surface 130 and the moveable latch piece 70 is moved to its at-rest position holding the cup 142 or cutter 144 against surface 130 and coaxially of shaft 12.

In specific embodiments, boss 122 has the above-identified dimensions to insure the coaxial-axial position of the tools 110, 112, 127, 129, 142, 144 on axis 22. In version 10, each slot is positioned on axis 22 within the tolerances of plus or minus 0.005 inches. Like version 10, the tools 127, 129, 142, 144 are positioned on version 120 coaxially of shaft 12 within tolerances of plus or minus 0.005 inch.

The improved tool driver 10 of the invention provides a new and improved tool driver which can be used with both acetabular reamer cups and patella cutters and other like rotary tools. By the improved tool driver of the invention these rotary tools may be driven about the longitudinal axis of shaft 12 with precision such that all of the cutting edges of the rotary tool will function as designed. Additionally, the improved tool driver of the invention can be used with rotary tools of all sizes, those which collect milled bone tissue and other debris for use as filler, those which do not. The new and improved tool driver invention can be easily cleaned, sterilized and reused as well as the rotary tools with which it is used.

While a specific embodiment of the invention has been shown and described herein for purposes of illustration, the protection afforded by any patent which may issue upon this application is not strictly limited to the disclosed embodiment; but rather extends to all structures and arrangements which fall fairly within the scope of the claims which are appended hereto:

What is claimed is:

1. A tool driver for connecting to a rotary tool having a back hole comprising a shaft having opposite ends and a longitudinal axis, a boss secured to said shaft at one of said ends by which said tool driver is connected to a rotary tool, a tool collet secured to said shaft at the other of said ends by which said tool driver is connected to a surgical hand piece, said boss having a distal end surface extending transversely of said axis and an exterior boss surface extending axially of said shaft, a flange between said boss and said shaft, said flange extending radially of said shaft outwardly a distance greater than said boss and having a flange surface facing in the same direction as said distal end surface, said boss being shaped and sized to be complementary to said back hole of a rotary tool, and a latch for holding said rotary tool onto said tool driver against said flange surface with said boss in said back hole thereof, whereby rotary tools of all sizes each are removably securable to said tool driver coaxially of said shaft.

2. The tool driver of claim 1 wherein said boss is coaxial of said shaft.

3. The tool driver of claim 1 wherein said boss cross-section taking transversely of said axis is circular.

4. The tool driver of claim 1 wherein said boss cross-section taking transversely of said axis is hexagonal.

5. The tool driver of claim 1 wherein said boss cross-section taking transversely of said axis is a parallelogram.

6. The tool driver of claim 1 wherein said boss has a maximum radial dimension less than the radial dimension of the rotary tool being used with said tool driver.

7. The tool driver of claim 1 wherein said flange is coaxial with said boss.

8. The tool driver of claim 1 wherein said flange is larger than said boss.

9. The tool driver of claim 1 wherein said latch includes a pin radially extending from said boss between said flange surface and said distal end surface.

10. The tool driver of claim 9 wherein said latch further comprises a latch slot in said boss opposite said pin, and a latch pin positioned within said latch slot and pivotally connected to said boss, said latch pin being moveable from a latched position in which said latch pin holds a rotary tool on said boss against said flange surface to a release position in which said rotary tool is positioned on and removed from said boss.

11. The tool driver of claim 1 wherein said latch includes a latch piece radially extending from said boss between said flange surface and said distal end surface.

12. The tool driver of claim 1 wherein said latch further comprises a latch slot in said boss, and a latch piece positioned within said latch slot and pivotally connected to said boss, said latch piece being moveable from a latched position in which said latch piece holds a rotary tool on said boss against said flange surface to a release position in which said rotary tool is positioned on and removed from said boss.

13. The tool driver of claim 1 wherein said latch further comprises a pair of diametrically opposed latch slots in said boss, and a latch piece positioned within each of said latch slots and pivotally connected to said boss, said latch pieces being moveable from a latched position in which latch pieces hold a rotary tool on said boss against said flange surface to a release position in which said rotary tool is positioned on and removed from said boss.

14. The tool driver of claim 13 wherein said latch piece is biased toward said latched position.

15. The tool driver of claim 10 wherein said latch piece is biased toward said latched position.

16. The tool driver of claim 12 wherein said latch piece is biased toward said latched position.

17. The tool driver of claim 12 further comprising an actuator, said actuator being slideably positioned on said shaft, a spring being positioned between said actuator and said shaft biasing said actuator toward said boss and said latch piece into said latched position.

18. The tool driver of claim 17 wherein said actuator has a latch slot therein forming a continuation of said boss latch slot, said latch piece being within said latch slot, said latch piece having a slot therein, said actuator having a follower in said slot, said follower moving within said slot when said actuator is moved between said latched position and said release position, said movement of said follower in said latch piece slot pivoting said latch piece from said latched position to said release position of said latch piece as said actuator moves away from said boss.

19. The tool driver of claim 12 further comprising an actuator, said actuator being slideably positioned on said shaft, a spring being positioned between said actuator and said shaft biasing said actuator toward said boss and said latch piece into said latched position.

20. The tool driver of claim 12 wherein said actuator has a latch slot therein forming a continuation of said boss latch slot, said latch piece being within said latch slot, said latch piece having a slot therein, said actuator having a follower in said slot, said follower moving within said slot when said actuator is moved between said latched position and said release position, said movement of said follower in said latch piece slot pivoting said latch piece from said latched position to said release position of said latch piece as said actuator moves away from said boss.

21. The tool driver of claim 9 further comprising a handle on said shaft, said handle being spaced from said boss by said actuator, said handle being rotatable about said axis independently of said shaft.

22. The tool driver of claim 1 wherein said latch further comprises a pair of diametrically opposed latch slots in said boss, and a latch piece positioned within each of said latch slots and pivotally connected to said boss, said latch pieces being moveable from a latched position in which said latch pieces hold a rotary tool onto said boss against said flange surface and to release position in which said rotary tool is positioned on and removed from said boss.

23. The tool driver of claim 22 further comprising an actuator, said actuator being slideably positioned on said shaft, a spring being positioned between said actuator and said shaft biasing said actuator toward said boss and said latch piece into said latched position.

24. The tool driver of claim 23 wherein said actuator has a latch slot therein forming a continuation of said boss latch slots, said latch pieces being within latch slots, said latch pieces having a slot therein, said actuator having a follower in said slot, said follower moving within said slot when said actuator is moved between said latched position, and said release position, said movement of said follower in said latch piece slots pivoting said latch pieces from said latched position to said release position of said latch pieces as said actuator moves away from said boss.

25. The tool driver of claim 24 further comprising a handle on said shaft, said handle being spaced from said boss by said actuator, said handle being rotatable about said axis independently of said shaft.

26. A tool for use with the tool driver of claim 9 having a cutting surface, an open back and a pair of diametrically opposite pin holes in said tool adjacent said back.

27. A tool for use with the tool driver of claim 1 having a cutting surface and a back with an opening therein free of structure, said opening being coaxial of said cutting surface and of a size and shape complementary of said boss of a tool driver.

28. The tool of claim 22 wherein said latch pieces are biased toward said latched position.

29. The tool of claim 12 wherein said latch piece is biased toward said latched position.

30. The tool of claim 10 wherein said latch pin is biased toward said latched position.

31. A tool having a cutting surface, an open back, a mounting bar having opposite ends extending diametrically across said open back, said mounting bar having opposite ends having a centrally located device thereon coaxial with said cutting surface half-way between the opposite ends of said diametral bar, said central device having surfaces thereon for engaging tool driver surfaces to position said tool and tool driver on the same axis of rotation.

* * * * *